United States Patent [19]

Drozd et al.

[11] Patent Number: 4,729,958

[45] Date of Patent: Mar. 8, 1988

[54] METHOD FOR IMPROVING THE FILTERABILITY OF A MICROBIAL BROTH

[75] Inventors: Jan W. Drozd; Andrew J. Rye, both of Sittingbourne, England

[73] Assignee: Shell Oil Company, Houston, Tex.

[21] Appl. No.: 807,940

[22] Filed: Dec. 12, 1985

[30] Foreign Application Priority Data

Dec. 14, 1984 [GB] United Kingdom ................ 8431653

[51] Int. Cl.$^4$ ............................................. C12N 1/08
[52] U.S. Cl. .................................... 435/270; 435/101; 435/104; 435/274; 435/910
[58] Field of Search ................... 435/270, 274, 91, 92, 435/101-104, 195, 196, 199, 243, 253-257, 259, 261, 262, 267, 270, 874, 276, 910

[56] References Cited

U.S. PATENT DOCUMENTS

| | | | |
|---|---|---|---|
| 3,488,256 | 1/1970 | High et al. | 435/270 |
| 3,496,065 | 2/1970 | Russell | 435/270 |
| 3,809,776 | 5/1974 | Chao | 426/431 |
| 3,867,255 | 2/1975 | Newell et al. | 195/5 |
| 3,887,431 | 6/1975 | Robbins et al. | 195/5 |
| 3,960,659 | 6/1976 | Fazakerley | 435/270 |
| 3,996,104 | 12/1976 | Lindblom et al. | 435/270 |
| 4,007,088 | 2/1977 | Fencl et al. | 435/270 |
| 4,010,071 | 3/1977 | Colegrove | 195/7 |
| 4,119,491 | 10/1978 | Wellington | 195/7 |
| 4,182,860 | 1/1980 | Naslund et al. | 435/104 |
| 4,326,037 | 4/1982 | Griffith et al. | 435/274 |
| 4,416,990 | 11/1983 | Rinaudo et al. | 435/104 |
| 4,431,734 | 2/1984 | Rinaudo et al. | 435/104 |
| 4,440,225 | 4/1984 | Holzwarth | 435/104 |
| 4,481,294 | 11/1984 | Downs | 435/259 |

OTHER PUBLICATIONS

Chemical Abstract, CA94(9): 63786x, citing S. African Patent No. 2A 78/6664 (30 Jul. 1980), to Merck and Co., Inc.

Atkinson, B. et al., *Biochemical Engineering and Biotechnology Handbook*, The Nature Press, N.Y. (1983), pp. 448-451, 1048-1057, 671-726.

Lehninger, A. L., *Principles of Biochemistry*, Worth Publishing Co., N.Y. (1982), pp. 54-55.

Davis, B. D. et al., *Microbiology*, Harper & Row, Publishers, Philadelphia (1980), pp. 154-161, 175-182.

Phillips, A. P., Biochim. Biophys. Acta, 195(1): 186-196 (1969).

*Primary Examiner*—Margaret Moskowitz

[57] ABSTRACT

Method of improving the filterability of a microbial broth containing microbial cell matter resulting from the breaking down of cells, which comprises contacting that broth with one or more enzymes having nuclease activity; use of the method for improving the flow of a microbial polysaccharide containing fluid displacement solution which is applied in enhanced oil recovery.

9 Claims, 6 Drawing Figures

METHOD FOR IMPROVING THE FILTERABILITY OF A MICROBIAL BROTH

BACKGROUND OF THE INVENTION

1. Field of the Invention

The present invention relates to a method for improving the filterability of a microbial broth and in particular of a broth which has been subjected to heating and/or clarification by an enzyme treatment and/or ultrafiltration and/or shear and/or storage. More in particular the broth is a fermentation broth of a polysaccharide producing microorgansim.

2. Description of the Prior Art

Polysaccharide polymers which are produced by fermentation of carbohydrates with suitable polysaccharide producing microorganisms are widely used as water thickeners. Especially in enhanced oil recovery operations they have established a utility as viscosity enhancers of displacement fluids. These displacement fluids are normally aqueous solutions which are pumped into an oil bearing rock formation to displace the oil from the reservoir rock.

Although displacement fluids containing polysaccharides such as those derived from *Xanthomonas campestris* are now widely used, still a major problem has not been completely solved. This problem concerns the presence of insoluble impurities in industrial grades of these polysaccharide solutions. In the typical commercial production of polysaccharides by e.g. Xanthomonas fermentation, the high viscosity of the fermentation broth precludes complete separation of insoluble material, such as cellular debris and nonviable bacteria from the polysaccharide-containing broth.

As a result, commercial grades of these microbial polysaccharides, i.e. xanthan gums, contain solids which do not dissolve when the xanthan gum is placed in dilute aqueous solution such as that required for polymer flooding in enhanced oil recovery. The presence of these particulate solids in the polysaccharide solution presents considerable difficulty in field application of the polymer flood because they can cause plugging of the rock face and injection water filters. Previous attempts to overcome this plugging problem have included caustic treatment of the polysaccharide solution and subsequent flocculation of the solids, enzyme treatment to bring about chemical decomposition of the solid material in the polysaccharide solution prior to use, and mechanical shear to break up the solids.

The treatment with enzymes of a polysaccharide aqueous solution to obtain a clarified solution has been widely described. From U.S. Pat. No. 4,010,071 a clarification of xanthan gum with a protease enzyme is known. The treatment with protease enzymes has also been described in U.S. Pat. No. 4,119,491. To improve the clarification an enzymatic disintegration is initiated. However before the cell bodies are completely disintegrated the solution is contacted with particles of solid siliceous material at an adsorption-enhancing pH followed by filtering-out the siliceous solids and the partially-disintegrated cell bodies that are adsorbed on them. In U.S. Pat. No. 4,416,990 corresponding to GB Pat. No. 2,085,904, a process is described for enzymatically purifying of a xanthan gum containing as impurities bacterial cell residues and microgels. This process comprises the treating of an aqueous dispersion of the gum with Basidiomycete cellulase.

In U.S. Pat. No. 4,326,037 corresponding to GB Pat. No. 2,065,688, a method is described for enhancing the ability of polysaccharides in aqueous solutions to flow through a porous medium which method comprises contacting the polysaccharides with an endoenzyme which is capable of hydrolyzing at least one of the linkages of the sugar units of the polysaccharides and maintaining the polysaccharides in contact with the enzyme under hydrolysis conditions for a time sufficient to decrease the tendency of the polysaccharides to plug the porous medium yet insufficient to decrease the viscosity of the aqueous polysaccharides by more than 25%.

Efforts are still being made to improve the filterability of a polysaccharide containing aqueous solutions. The term filterability is commonly used to describe the ability of a fluid to flow through a porous medium, and derives from the filtration test employed in the oil industry. From U.S. Pat. No. 4,431,734 corresponding to GB Pat. No. 2,099,008, an enzymatic process is known for the treatment of xanthan gums for improving the filterability of their aqueous solutions. In this process a combination of two enzymes i.e. a polysaccharase and protease is used.

SUMMARY OF THE INVENTION

It has now been found that the filterability of a polysaccharide containing broth which has been subjected to heating and/or clarification by an enzyme treatment and/or ultrafiltration and/or shear and/or storage can surprisingly be further improved if the broth is contacted with one or more enzymes having nuclease activity. Further investigation has revealed that a treated microbial broth contains besides a majority of intact cells, cellular matter released from a number of cells which has been wholly or partially broken down. Having surprisingly found that nucleases improve the filterability of a microbial cell matter containing aqueous solution, it is now thought that disintegration by nuclease enzymes of Deoxyribonucleic acid (DNA) and Ribonucleic acid (RNA) which are released from cells which break down might have an enhancing effect on the filterability of the microbial broth. In this respect it is remarkable that the filterability of such a broth can be greatly improved even when DNA and/or RNA are present in only very low concentrations e.g. as in the case of an enzyme treated and ultrafiltered broth. Further it is an advantage of the present process that the viscosity of e.g. a microbial polysaccharide broth which is treated with nuclease enzymes hardly decreases. Therefore the present invention provides a method for improving the filterability of a microbial containing cell matter resulting from the breaking down of cells, which comprises contacting that broth with one or more enzymes having nuclease activity. In this patent application the term "microbial broth" refers not only to a fermentation broth but also to aqueous solutions and aqueous/non aqueous dispersions of e.g. polysaccharides derived from such a fermentation broth, which contain minor amounts of nucleic acids. In particular the present method is highly suitable for improving the filterability of a broth of a polysaccharide producing microorganism. Therefore the present method is preferably applied to that kind of microbial broth.

Figure 1:
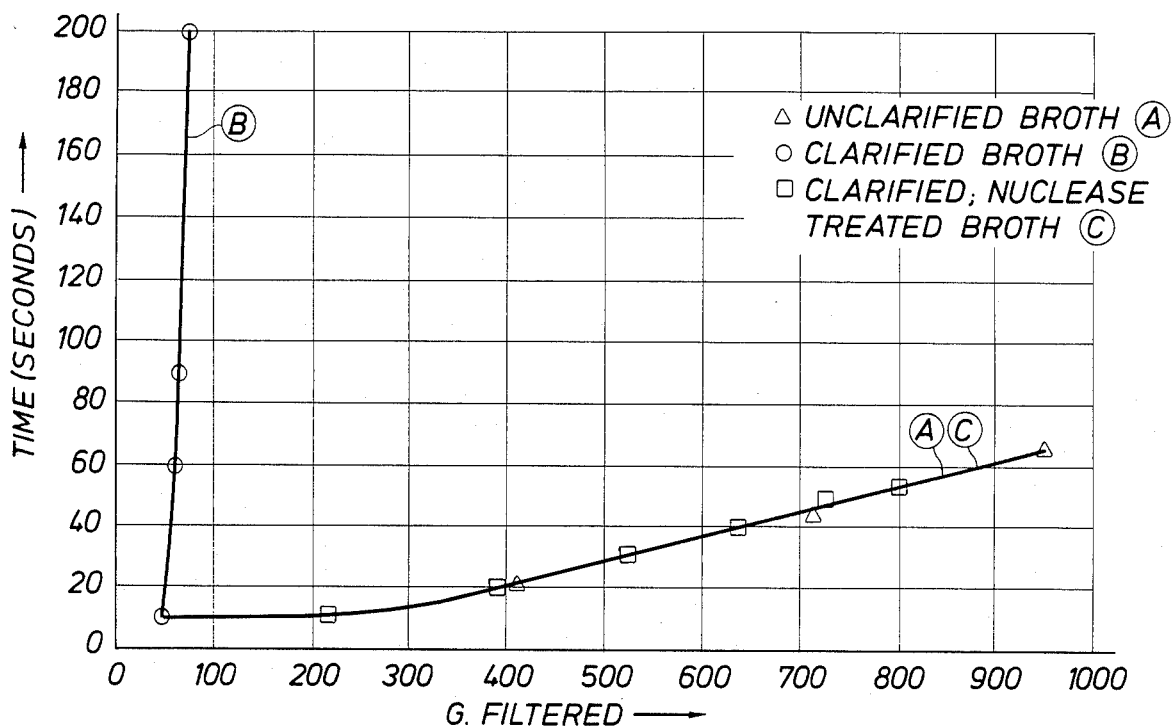
FIG. 1. A filterability plot for Example I which shows the untreated broth (A) has good filterability but filterabilitiy of the clarified broth (B) is much worse and nuclease treatment of the clarified broth (C) restores the original filterabilty.

The microbial broth which is treated with the present method has preferably been first subjected to a clarification with a protease or any other agent which gives cell lysis, and/or ultrafiltration. The enzyme having nuclease activity is preferably Deoxyribonuclease and/or Ribonuclease. Since Deoxyribonuclease gives a greater filterability improvement it is preferably used. Enzymes which have been contaminated with nuclease activity may also be suitably used and are therefore within the scope of the present invention. Enzymes which may have been contaminated with nuclease activity are e.g. proteases, lipases, cellulases, polysaccharases and the like. The microorganism which forms the microbial broth is preferably selected from the group consisting of *Xanthomonas campestris* NCIB 11803, NCIB 11854, Pseudomonas sp. NCIB 11592, NCIB 11264, *Agrobacterium tumefaciens/Agrobacterium radiobacter* NCIB 11883.

The temperature at which the microbial broth is contacted with the nuclease is preferably in the range of 5°-95° C. To enhance the effect of the nuclease treatment the microbial broth is preferably subjected to a mixing-treatment after contacting the broth with nuclease.

Preferably per 0.1-10 grams (dry weight) bacteria per liter broth or up to 60 grams (dry weight) bacteria per liter concentrate an amount of 0.0001-250 milligrams nuclease per liter broth or concentrate is used.

Cells may contain their own nuclease activity. However, they may also be genetically or physiologically modified to induce or enhance this nuclease activity. Microorganisms which have this inbuilt ability of releasing nuclease may obviate the necessity of using nuclease enzyme when filterability of their broths have to be improved.

As indicated before the method according to the present invention may be used to improve the filterability of any polysaccharide aqueous solution whether a broth or a more purified aqueous solution such as one can obtain from a polysaccharide containing broth which has been subjected to an ultrafiltration and/or enzyme treatment as described in European Pat. No. 49,012 in the name of Applicant. Polysaccharide aqueous solutions, which have been obtained from a polysaccharide fermentation broth which has been treated with enzymes and subsequently subjected to ultrafiltration, have found a particular use in e.g. enhanced oil recovery operations and in the formulation of water-in-oil emulsions as described in European Pat. No. 137,538 both unpublished patent applications in the name of Applicant.

Especially where it concerns the use in fluid displacement solutions for enhanced oil recovery the aqeous polysaccharide concentrate which has a concentration of about 8-10wt% may be preferably treated with the present process. Also the flow of the aqueous fluid displacement solution through a porous medium which solution is made by dilution of the aqueous polysaccharide concentrate with water can be improved with the present method. In practice the water is sea water or water which is available at the oil reservoir where the fluid displacement solution has to be used.

Therefore the present invention further provides a method for improving the flow of a microbial polysaccharide containing aqueous fluid displacement solution through a porous medium.

The present invention will be further described with reference to the following Examples.

EXAMPLE I

To demonstrate filterability impairment on broth clarification by protease treatment and subsequent improvement in filterability by nuclease treatment of the clarified broth the following experiment was carried out.

A broth of *Xanthomonas campestris* NCIB 11854 containing 3.50 g dry wt bacteria per liter and 11.15 g dry wt polymer per liter was clarified as follows. To 300 g of broth at pH 7.0±0.2 in a 500 ml flask was added protease (Novo 0.6 L Alcalase) to 0.25 g.l$^{-1}$. The flask contents were mixed by hand shaking for 30 seconds and then incubated statically in a water bath at 55° C. for 2½ hours. Over this period the optical density of the broth (as measured after approximately 20-fold dilution in water) in a 1 cm cuvette at 600 nm fell from 5.5 to 0.90. This clarified broth was cooled to 30° C. when the pH was 7.3. It was divided into two halves in 250 ml flasks and to one half were added the following nucleases: Sigma Ribonuclease-A R-5503 to 50 mg l$^{-1}$, Sigma Deoxyribonuclease-1 D-0876 to 48 mg l$^{-1}$ and Sigma Deoxyribonuclease-1 D-4638 to 93 mg l$^{-1}$. Both flasks were then incubated at 30° C., 200 rpm on an orbital shaker, together with a flask containing unclarified broth, for 1 hour, and then stored at +4° C. Filterability testing was done on (A) unclarified broth, (B) clarified broth and (C) clarified broth treated with nucleases. 45 g samples of broth were diluted to 500 g in substitute ocean water at 30° C. to give 1.0 g l$^{-1}$ polymer.

Substitute Ocean Water pH 8.2 made up to 1.0 liter in distilled water and filtered through a 0.22 μM filter before use.

| Compound | Conc g/l |
|---|---|
| NaCl | 24.53 |
| MgCl$_2$ | 5.20 |
| Na$_2$SO$_4$ | 4.09 |
| CaCl$_2$ | 1.16 |
| KCl | 0.695 |
| NaHCO$_3$ | 0.201 |
| KBr | 0.101 |
| H$_3$BO$_3$ | 0.027 |
| SrCl$_2$ | 0.025 |

| -continued | |
| --- | --- |
| Compound | Conc g/l |
| NaF | 0.003 |
| Ba(NO$_3$)$_2$ | 0.0000994 |
| Mn(NO$_3$)$_2$ | 0.0000340 |
| Ca(NO$_3$)$_2$ | 0.0000308 |
| Zn(NO$_3$)$_2$ | 0.0000151 |
| Pb(NO$_3$)$_2$ | 0.00000049 |

The 500 g samples were mixed for the short time of 30 seconds in a Waring Commercial blender. Filterability was then performed through a Millipore 1.2 μM mean pore size RA filter, 47 mm diameter, at 40 psi, 30° C. FIG. 1 indicates the untreated broth (A) has good filterability but filterability of the clarified broth (B) is much worse. However, nuclease treatment of the clarified broth (C), restores the original filterability.

There was very little difference between the viscosity of the samples (1.0 g $l^{-1}$ polymer in substitute ocean water, 30° C., measured at 7.34 $S^{-1}$ in a Brookfield LVT hanging bob viscometer).

Unclarified Broth: 50 cP
Clarified Broth: 47 cP
Clarified, nuclease treated Broth: 50 cP This example clearly indicates that nuclease (DNA-'ase plus RNA'ase) treatment of clarified broth greatly improves its filterability.

EXAMPLE II

The following experiment shows that heating of a xanthan broth results in a deterioration in filterability which can be subsequently improved by nuclease treatment. A broth of *Xanthomonas campestris* NCIB 11854 was produced which contained (g.dry wt. per liter), bacteria 2.63, polysaccharide 11.45. The broth had a pH of 7.1±0.2; 500 g was incubated in a 2-liter flask at 55° C., 220 rpm on an orbital shaker for 4½ hours. Over this period the optical density measured as in Example (II) at 600 nm fell from 5.7 to 2.5 which indicated some cell lysis had taken place. When cooled to 30° C. two 120 g amounts of this product were put in separate 250 ml flasks. To one flask were added the following nucleases: Sigman Ribonuclease-A, R-5503 to 8 mg $l^{-1}$, Sigma Deoxyribonuclease-1, R-4638 to 6 mg $l^{-1}$ and Sigma Deoxyribonuclease-1, R-0876 to 4 mg $l^{-1}$. These two flasks, plus a flask with 120 g of non-heated broth, were incubated at 30° C., 200 rpm on an orbital shaker for 1½ hours and then stored at +4° C.

Figure 2:
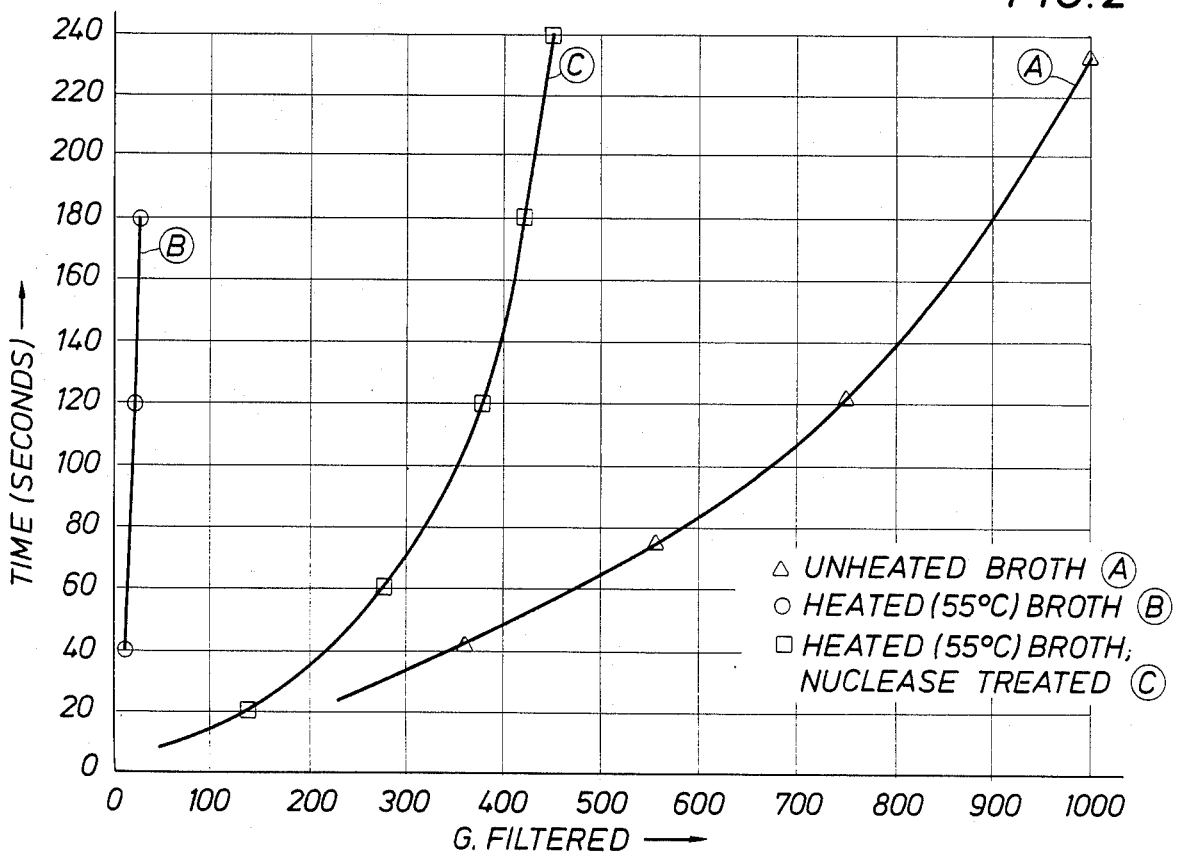
FIG. 2. A filterability plot for Example II which shows the results and indicates that the heat treatment impairs filterability (B) but subsequent nuclease treatment (C) improves filterability.

Filterability of the broths at 1.0 g polysaccharide per liter was measured as in Example (II). FIG. 2 shows the results and indicates that heat treatment impairs filterability (B) but subsequent nuclease treatment (C) improves filterability, although in this examle not to the level of the unheated broth (A) but when the nuclease concentrations used were increased and time of treatment lengthened filterability of the heated broth was further improved. The viscosities (as measured in Example I) at 7.34 $S^{-1}$ of (A), (B), and (C) were 55 cP, 48 cP and 48 cP respectively (at 1 g polysaccharide per liter in substitute ocean water) which indicated no major changes in viscosity had taken place during the treatments.

EXAMPLE III

Figure 3:
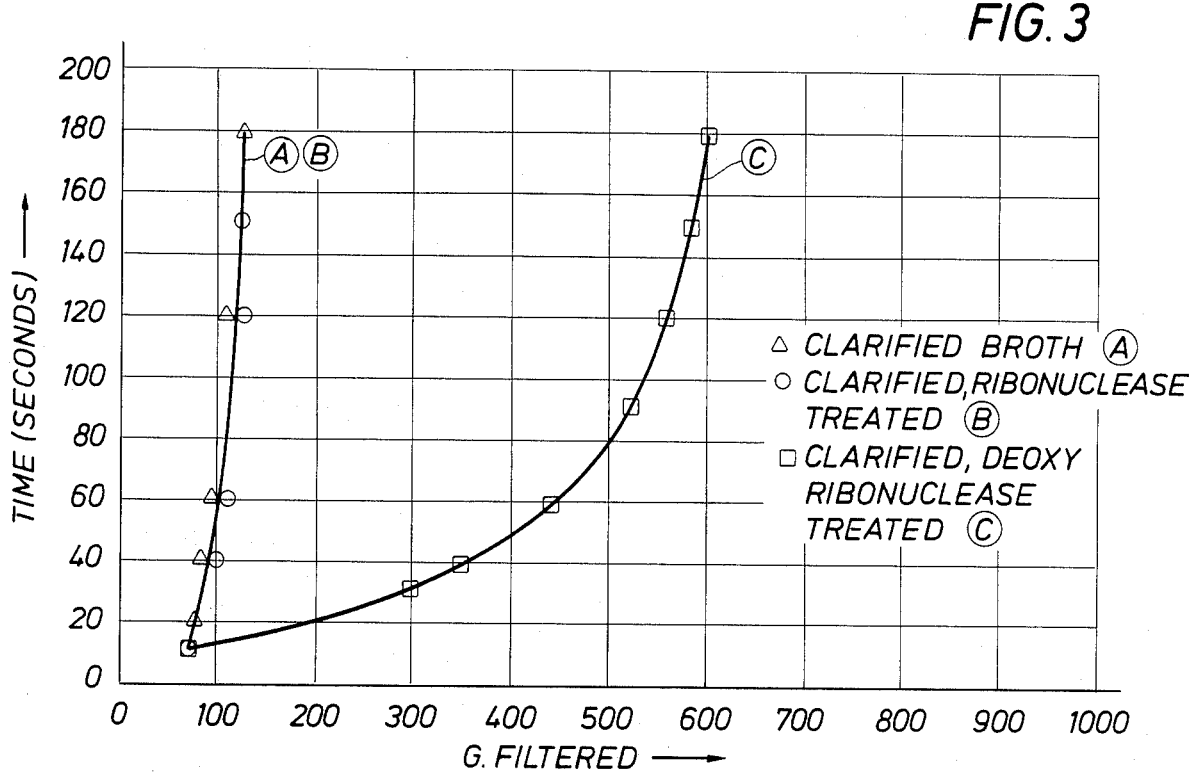
FIG. 3. A filterability plot for Example III which shows that the major improvement in filterability of the clarified broth is given by deoxyribonuclease rather than ribonuclease treatment.

This example demonstrates that Deoxyribonuclease gives a better filterability improvement than Ribonuclease. A xanthan broth as in Example (II) was clarified as follows. To 500 g of broth in a 2-liter baffled flask protease (Novo 0.6 L Alcalase) was added to 0.30 g $l^{-1}$ and the flask was incubated at 55° C. for 4½ hours on an orbital shaker at 220 rpm. Over this period the optical density of the broth as measured at 600 nm in a 1 cm cuvette (sample diluted approximately 20-fold in distilled water) fell from 5.7 to 0.42. The pH of the clarified broth was 7.0±0.2 at 30° C. Three 120 g samples of clarified broth were then put in 250 ml flasks and treated as follows: to one flask (A), no additions were made, to the second flask (B), Sigma Ribonuclease-A R-5503 was added to 37 mg $l^{-1}$, and to flask (C) was added Sigma Deoxyribonuclease 1, D-4638 to 28 mg $l^{-1}$. The flasks were incubated at 30° C., 220 rpm on an orbital shaker for 4 hours and stored at +4° C. Filterability of these products was then tested in substitute ocean water at 30° C. as described in the previous examples. FIG. 3 clearly indicates that the major improvement in filterability of the clarified broth is given by deoxyribonuclease rather than ribonuclease treatment. The viscosities (as measured in Example I) showed no major changes during the various treatments and were (at 7.34 $S^{-1}$, 30° C., 1 g polysaccharide per liter in substitute ocean water) 47 cP for (A), 52 cP for both (B) and (C).

EXAMPLE IV

This example demonstrates that impairment of filterability by high molecular weight DNA is not specific to the cellulose acetate/nitrate filterss used. This was done because it is known that certain forms of nucleic acid, especially of DNA will bind to cellulose nitrate filters and the Millipore RA filters used in the filterability testing are mixed cellulose acetate/nitrate filters.

A *Xanthomonas campestris* NCIB 11854 broth containing 11.5 g dry wt polysaccharide per liter and 2.5 g dry wt bacteria per liter was clarified as follows. 1.25 kg of broth, pH 6.8±0.2, was placed in a 2.0 liter baffled flask and protease (Novo 0.6 L Alcalase) was added to 0.20 g per liter. The flask was incubated at 55° C. for 4.75 hours at 56° C. on an orbital shaker at 200 rpm. During clarification the optical density (measured as in Example I) decreased from 3.6 to 0.60. The clarified broth was cooled to 30° C. 120 g amounts of clarified broth were placed into each of two 250 ml flasks. To one was added the following nucleases: Sigma Ribonuclease-A R-5503 to 21 mg per liter, Sigma Deoxyribonuclease 1, D-4638 to 19 mg per liter, Sigma Deoxyribonuclease 1, D-0876 to 8 mg per liter and Sigma Deoxyribonuclease 11, D-8764 to 3 mg per liter. The flasks were incubated at 30° C., 220 rpm on an orbital shaker for 3.75 hours and then stored at +4° C.

Figure 4:
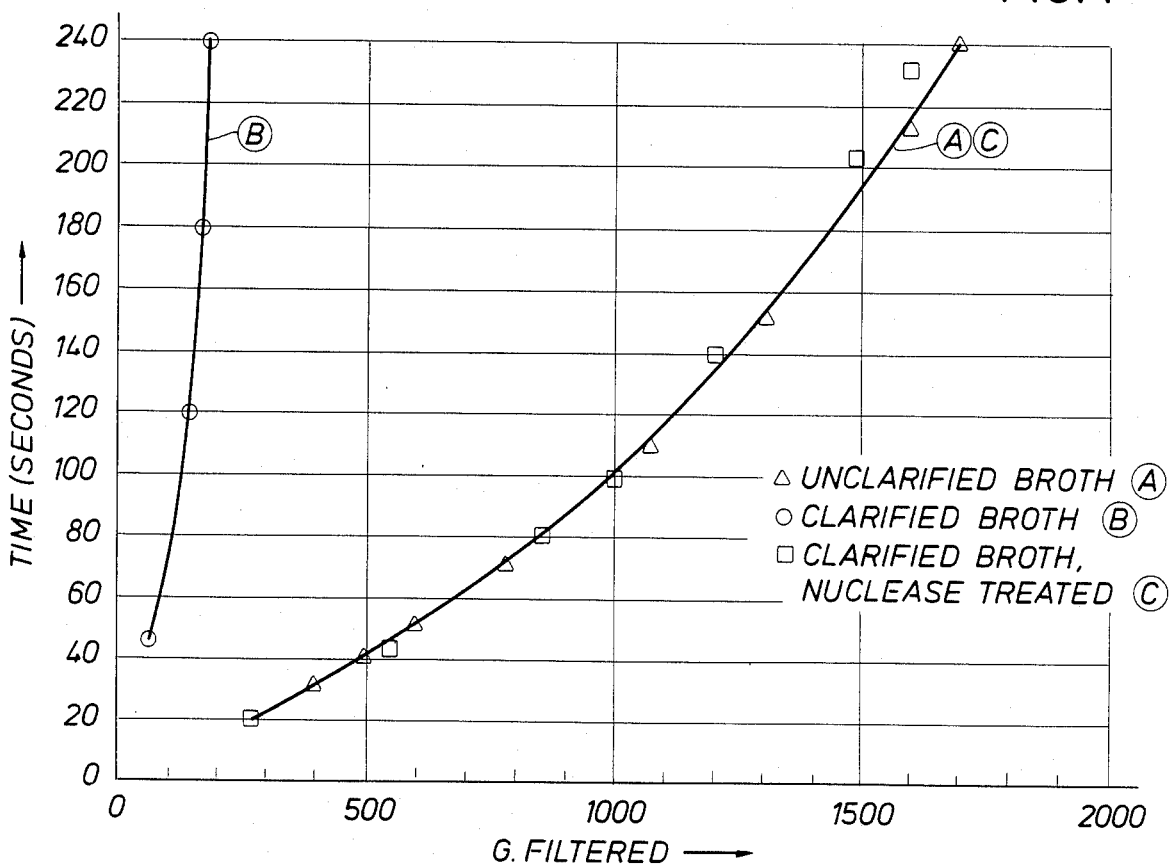
FIG. 4. A filterability plot for Example IV which shows the clarified broth (B) blocks the filter, but nuclease treatment (C) restores filterability to that of the untreated broth (A).
Figure 5:
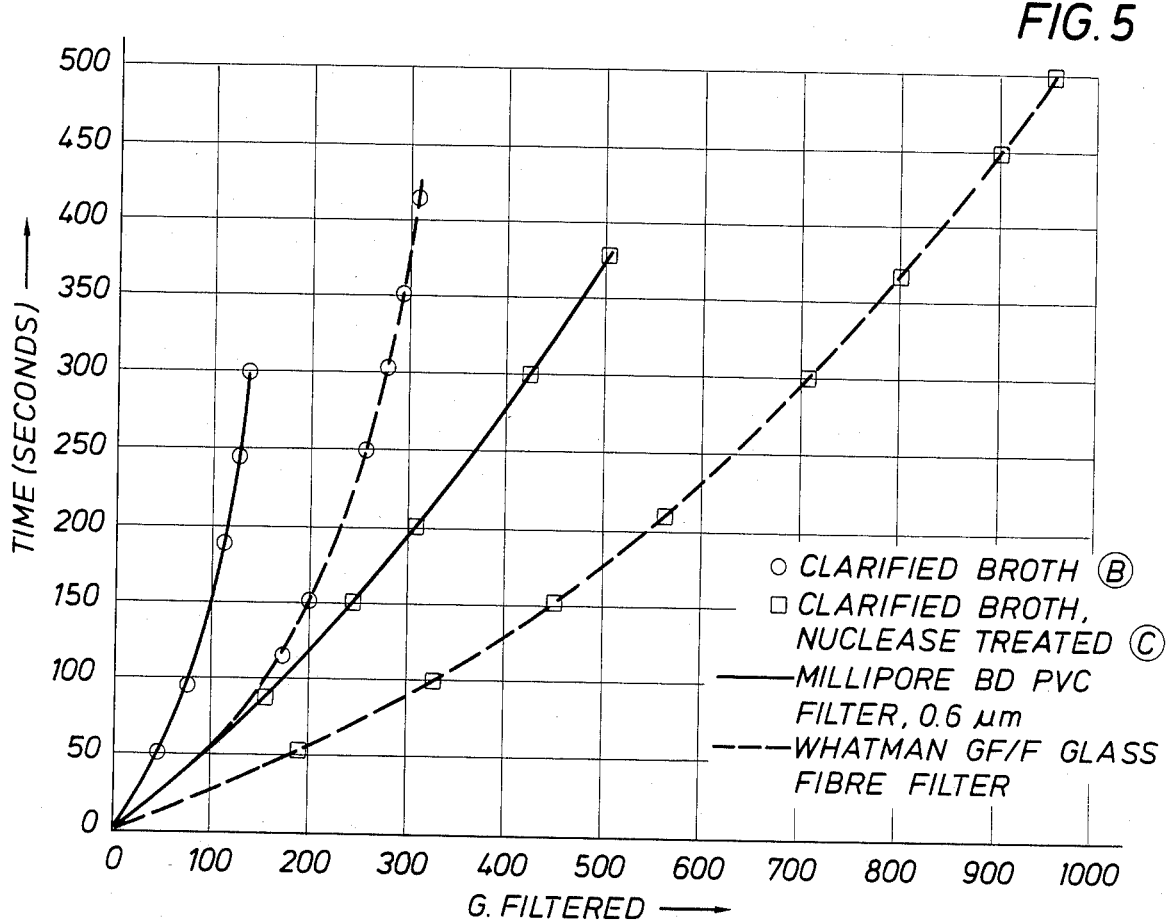
FIG. 5. A filterability plot for Example IV which shows that the filterability of the nuclease-treated clarified broth (C) was much better than that of the non-nuclease, clarified broth, (B).

Filterability was measured as in Example (I) at 30° C. in substitute oean water through a Millipore RA 1.2 μM mean pore size filter. FIG. 4 shows the clarified broth (B) blocks the filter, but nuclease treatment (C) restores filterability to that of the untreated broth (A). To check on filtration through different membranes the nuclease-treated, (C), and non-nuclease treated, (B), clarified broths were filtered (with the same conditions as previously) through Millipore Polyvinylchloride membranes BD, 0.6 μM mean pore size, 47 mm diameter (FIG. 5) and also through Whatman GF/F glass fibre filters, 47 mm diameter (FIG. 5). In both cases filterability of the nuclease-treated clarified broth (C) was much better than that of the non-nuclease, clarified broth, (B). Thus the impairment of filterability by high molecular weight nucleic acid is not specific to cellulose acetate/nitrate filters. The viscosities of the variously treated broths were very similar: (A) was 69 cP, (B) was 63 cP and (C) was 62 cP as measured in Example (I). This indicated that nuclease treatment had not altered product viscosity.

EXAMPLE V

Figure 6:
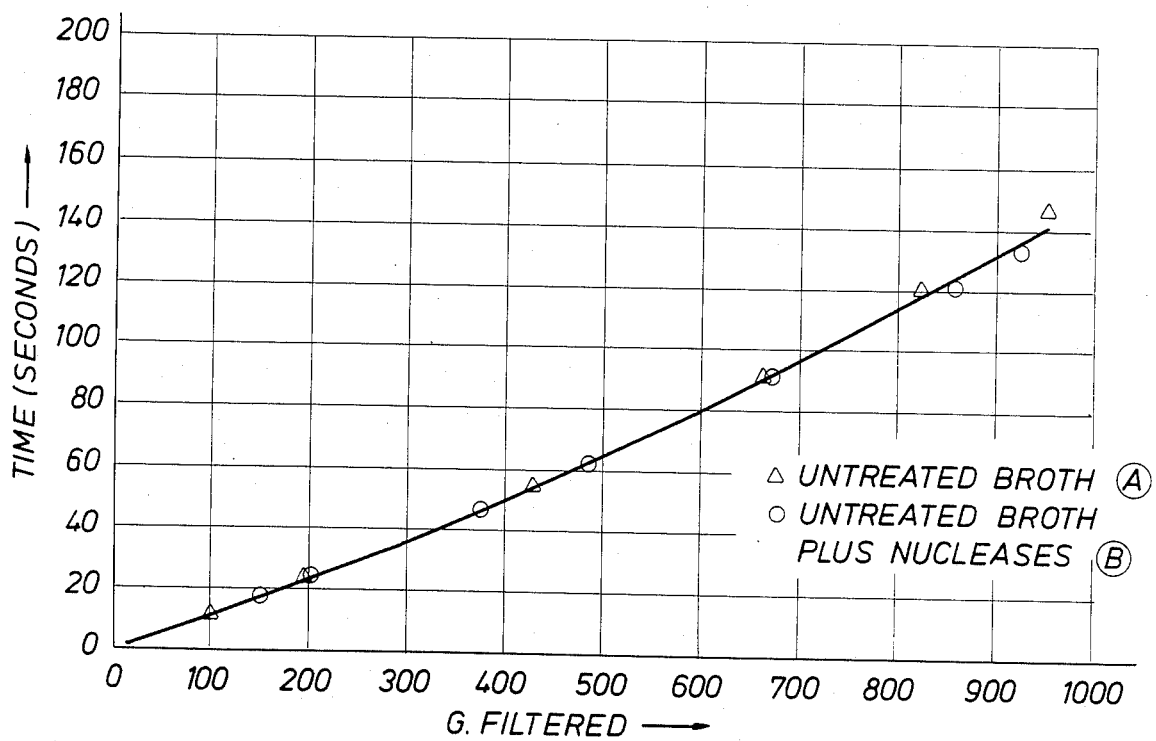
FIG. 6. A filterability plot for Example V which shows no differences between the filterability of the nuclease-treated, (B), and non nuclease-treated, (A), xanthan broths.

In this example it is demonstrated that nuclease treatment does not improve the filterability of a broth that has not been treated e.g. heated, sheared, stored or clarified. A fresh *Xanthomonas campestris* NCIB 11854 broth, pH 6.90±0.10, containing 3.50 g. dry wt. liter$^{-1}$ bacteria and 11.2 g. dry wt. liter$^{-1}$ polymer was treated as follows. Two 300 g. amounts were placed in each of two 500 ml. flasks. To one flask (A) no additions were made, while to the other flask (B), the following nucleases were added: 'Sigma' Ribonuclease A, R-5503, 0.0043 g; Sigma Deoxyribonuclease-1, D-4638, 0.0033 g. and 'Sigma' Deoxyribonuclease-1, D-0876, 0.0024 g. Both flasks were incubated at 30° C. for 5.25 hours, 200 r.p.m. on an orbital shaker. 1.2 µM filtration tests were then performed as in Example (I) at 1.0 g. polymer liter$^{-1}$ at 30° C. in substitute ocean water. FIG. 6 clearly shows no differences between the filterability of the nuclease-treated, (B), and non-nuclease treated, (A), xanthan broths.

What is claimed is:

1. A method of preparing an aqueous microbial polysaccharide-containing broth of improved filterability which comprises: (a) fermenting microorganisms selected from the group consisting of xanthan-producing species of Xanthomonas, Pseudomonas and Agrobacterium to obtain an aqueous microbial broth comprising polysaccharide polymers produced by said microorganisms and microbial cell matter; (b) subjecting said broth to a treating step which results in the breaking down of said microbial cell matter; and (c) contacting said broth with one or more enzymes having nuclease activity for a time and under conditions sufficient to increase the filterability of said broth.

2. A process for preparing an aqueous microbial polysaccharide-containing broth of improved filterability from an aqueous microbial broth comprising microbial polysaccharide polymers produced by a microorganism selected from the group consisting of Xanthomonas, Pseudomonas, or Agrobacterium, and broken microbial cell matter, which process comprises subjecting said aqueous microbial broth, comprising polysaccharide polymr and broken microbial cell matter, to treatment with one or more enzymes having nuclease activity for a time and under conditions sufficient to increase the filterability of said broth.

3. A method according to claim 2 in which the microbial broth has previously been subjected to a clarification with a protease or an other agent which causes cell lysis, or ultrafiltration.

4. A method according to claim 3 in which the enzyme having nuclease activity is a Deoxyribonuclease or a Ribonuclease.

5. A method according to claim 4 in which the enzyme is Deoxyribonuclease.

6. A method according to claim 5 in which the microorganism is selected from the group consisting of *Xanthomonas campestris* NCIB 11803, NCIB 11854, Pseudomonas sp. NCIB 11592, NCIB 11264 and *Agrobacterium tumefaciens/Agrobacterium radiobacter* NCIB 11883.

7. A method according to claim 5 in which the microbial broth is contacted with the nuclease at a temperature in the range of 5°-95° C.

8. A method according to claim 5 in which 0.1-10 grams dry weight bacteria per liter broth or up to 60 grams dry weight bacteria per liter concentrate of said broth is contacted with an amount of 0.0001-250 milligrams nuclease per liter of broth or concentrate.

9. A process according to claim 5 in which the microorganism is *Xanthomonas campestris*.

* * * * *